(12) United States Patent
Kadota et al.

(10) Patent No.: US 8,304,567 B2
(45) Date of Patent: Nov. 6, 2012

(54) ORGANORUTHENIUM COMPLEX, AND METHOD FOR PRODUCTION OF RUTHENIUM THIN FILM USING THE RUTHENIUM COMPLEX

(75) Inventors: Takumi Kadota, Ube (JP); Chihiro Hasegawa, Ube (JP); Hiroki Kanato, Ube (JP); Hiroshi Nihei, Ube (JP)

(73) Assignee: Ube Industries, Ltd, Ube-shi, Yamaguchi (JP)

( * ) Notice: Subject to any disclaimer, the term of this patent is extended or adjusted under 35 U.S.C. 154(b) by 664 days.

(21) Appl. No.: 12/375,278

(22) PCT Filed: Jul. 26, 2007

(86) PCT No.: PCT/JP2007/064713
§ 371 (c)(1),
(2), (4) Date: Nov. 12, 2009

(87) PCT Pub. No.: WO2008/013244
PCT Pub. Date: Jan. 31, 2008

(65) Prior Publication Data
US 2010/0055313 A1 Mar. 4, 2010

(30) Foreign Application Priority Data

Jul. 27, 2006 (JP) ................. 2006-205402
Aug. 30, 2006 (JP) ................. 2006-233225
Aug. 30, 2006 (JP) ................. 2006-233226
Nov. 15, 2006 (JP) ................. 2006-308812
Dec. 15, 2006 (JP) ................. 2006-338003
Jan. 18, 2007 (JP) ................. 2007-008680

(51) Int. Cl.
*C07F 15/00* (2006.01)
*C23C 16/00* (2006.01)
(52) U.S. Cl. .............. 556/41; 427/248.1; 427/255.28
(58) Field of Classification Search ............ 556/41; 427/248.1, 255.28
See application file for complete search history.

(56) References Cited

U.S. PATENT DOCUMENTS

| | | | |
|---|---|---|---|
| 6,303,809 B1 | 10/2001 | Chi et al. | |
| 6,605,735 B2 | 8/2003 | Kawano et al. | |
| 6,743,934 B2 | 6/2004 | Saito et al. | |
| 7,595,414 B2 * | 9/2009 | Kadota et al. | 556/40 |
| 2003/0203102 A1 * | 10/2003 | Saito et al. | 427/132 |

FOREIGN PATENT DOCUMENTS

| | | |
|---|---|---|
| JP | 2003-306472 A | 10/2003 |
| JP | 2003-342286 A | 12/2003 |
| JP | 2005-023379 A | 1/2005 |
| JP | 2006-241557 A | 9/2006 |
| WO | WO 2005/087697 * | 9/2005 |
| WO | WO 2005/087697 A1 | 9/2005 |

OTHER PUBLICATIONS

European Search Report for EP 07 79 1413 (PCT/JP2007064713) mailed Mar. 16, 2011.
Powell, P. 1974 "Synthesis of some 1,5-cyclooctadiene-ruthenium(II) complexes" *J Organometallic Chem* 65:89-92.
Fröhlich, F. et al. 2001 "Growth of Ru and $RuO_2$ films by metal-organic chemical vapour deposition" *J Phys IV France* 11:Pr3-325-332.
Notification of Transmittal of Translation of the International Preliminary Report on Patentability, mailed Feb. 5, 2009.

* cited by examiner

*Primary Examiner* — Porfirio Nazario Gonzalez
(74) *Attorney, Agent, or Firm* — Nixon Peabody LLP; Jeffrey L. Costellia

(57) ABSTRACT

An organoruthenium complex represented by the general formula (1-1), bis(acetylacetonato)(1,5-hexadiene)ruthenium and bis(acetylacetonato)(1,3-pentadiene)ruthenium have low melting points, show excellent stability against moisture, air and heat, and are suitable for the film formation by a CVD method. (1-1) wherein X represents a group represented by the general formula (1-2); Y represent a group represented by the general formula (1-2) or a linear or branched alkyl group having 1 to 8 carbon atoms; Z represents a hydrogen atom or an alkyl group having 1 to 4 carbon atoms; and L represents an unsaturated hydrocarbon compound having at least two double bonds: (1-2) wherein $R^a$ and $R^b$ independently represent a linear or branched alkyl group having 1 to 5 carbon atoms.

33 Claims, 1 Drawing Sheet

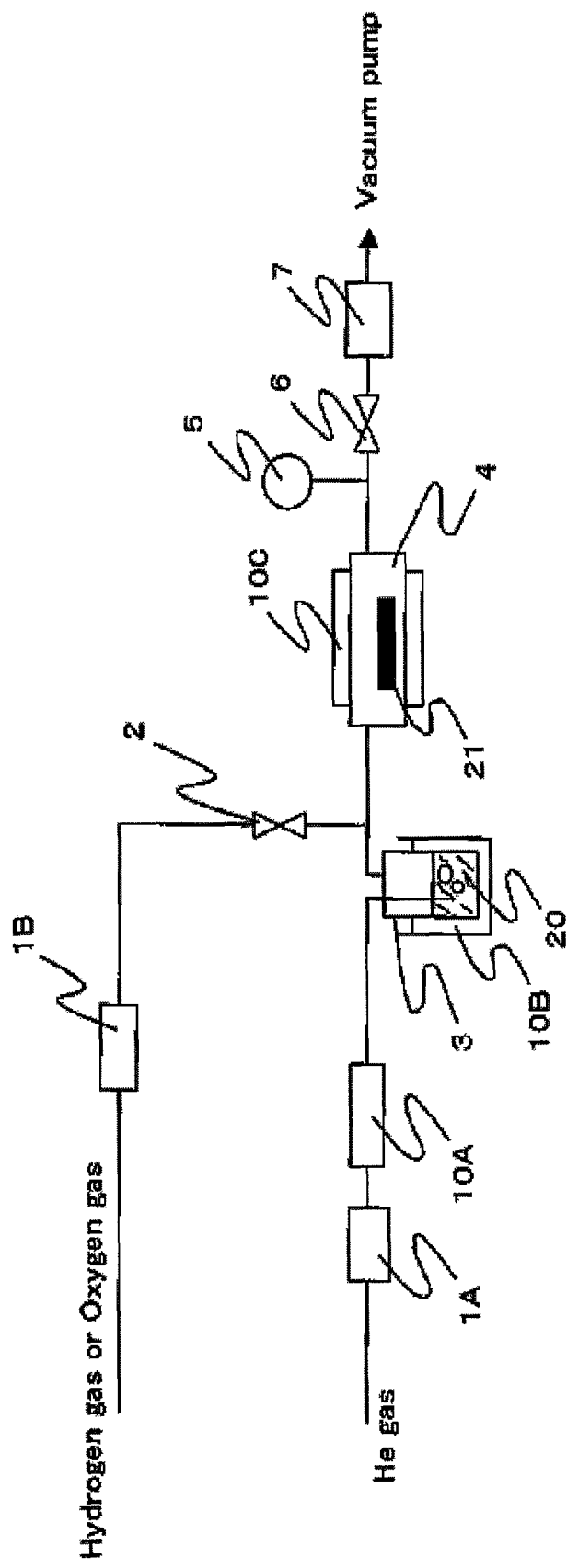

ORGANORUTHENIUM COMPLEX, AND METHOD FOR PRODUCTION OF RUTHENIUM THIN FILM USING THE RUTHENIUM COMPLEX

This application is U.S. National Phase of International Application PCT/JP2007/064713, filed Jul. 26, 2007 designating the U.S., which claims priority to Japanese Patent Application No. 2006-205402 filed Jul. 27, 2006, Japanese Patent Application No. 2006-233225, filed Aug. 30, 2006, Japanese Patent Application No. 2006-233226, filed Aug. 30, 2006, Japanese Patent Application No. 2006-308812, filed Nov. 15, 2006, Japanese Patent Application No. 2006-338003, filed Dec. 15, 2006 and Japanese Patent Application No. 2007-008680, filed Jan. 18, 2007.

TECHNICAL FIELD

The present invention relates to an organoruthenium complex which can be used for forming a ruthenium thin film. The present invention also relates to a method for producing a ruthenium thin film, particularly a metallic ruthenium-containing thin film, by a chemical vapor deposition method (hereinafter, referred to as a CVD method) using the organoruthenium complex.

BACKGROUND ART

In recent years, several studies have been conducted on the use of metallic ruthenium or ruthenium oxide as a material for a thin film electrode of a semiconductor device such as a DRAM due to their excellent electrical properties such as a specific resistance value. Metallic ruthenium, in particular, has better electrical properties than ruthenium oxide, and therefore is a desirable material for a thin film electrode of a semiconductor device. These ruthenium-containing thin films are most commonly formed by a CVD method, for example, because the CVD method can easily give a uniform thin film. Therefore, there is a need for a raw material compound suitable for the formation of a ruthenium-containing thin film by a CVD method.

A ruthenium complex having a β-diketonato or cyclopentadienyl derivative as a ligand, for example, is beginning to be widely used as a material for forming a thin film containing a ruthenium atom by a CVD method. The ruthenium complex having the above-mentioned ligand has good stability and sublimability, and therefore is useful as a ruthenium source for the CVD method.

Specifically, there has been disclosed a method for producing a mixed film of a metallic ruthenium thin film and a ruthenium oxide thin film, i.e. a film comprising a metallic ruthenium phase and a ruthenium oxide phase, by a CV) method, by reacting a β-diketonato ruthenium complex having a diene compound as a ligand with a β-diketonato ligand (see Non-Patent Document 1, for example. Incidentally, some of these complexes are known compounds, but are solid at ordinary temperature.) with an oxygen gas at a high temperature (see Patent Document 1 and Non-Patent Document 2, for example.). In this method, however, owing to the use of the oxygen gas, the mixing of ruthenium oxide, which has a much higher specific resistance value than metallic ruthenium, may be inevitable. In addition, owing to the high film-forming temperature, an impurity atom such as a carbon atom or the like may be mixed into the obtained ruthenium thin film, leading to the reduction of the specific resistance value.

There has been also disclosed a method for producing a metallic ruthenium thin film by a CVD method, by reacting a ruthenium complex having a β-diketonato and a carbonyl as a ligand with hydrogen at a high temperature (see Patent Document 2, for example.). According to this method, however, ruthenium oxide may be mixed in the obtained ruthenium thin film, leading to the reduction of the specific resistance value, although a hydrogen gas is used. (The oxygen content in the obtained ruthenium thin film is 2 to 3%.)

Furthermore, Patent Document 3 discloses a ruthenium complex comprising a β-diketonato having an alkoxyalkylmethyl group as a ligand, as a material for forming a thin film by a CVD method. None of the ruthenium complexes disclosed herein has a diene compound as a ligand.

LIST OF REFERENCES

Patent Document 1: JP-A-2003-306472
Patent Document 2: U.S. Pat. No. 6,303,809 B1
Patent Document 3: WO 2005/087697 A1
Non-patent Document 1: J. Organomet. Chem., 65, 89 (1974)
Non-patent Document 2: J. Phys. IV France, 11, Pr3-325 (2001)

DISCLOSURE OF THE INVENTION

Problems to be Solved by the Invention

An object of the present invention is to provide an organoruthenium complex which has a low melting point, excellent stability against moisture, air and heat, and is suitable for the film formation by a CVD method in order to solve the above-mentioned problems. Another object of the present invention is to provide a method for producing a ruthenium-containing thin film using the organoruthenium complex.

Another object of the present invention is to provide a method for producing a metallic ruthenium-containing thin film which does not comprise a ruthenium oxide, using the above ruthenium complex or other ruthenium complexes, by a chemical vapor deposition method.

Means for Solving the Problems

The present invention relates to the following matters:

[1] An organoruthenium complex comprising a β-diketonato having an alkoxyalkylmethyl group and an unsaturated hydrocarbon compound having at least two double bonds as a ligand, and represented by the general formula (1-1):

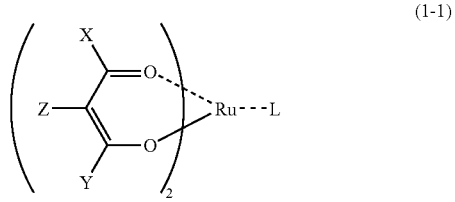

wherein X represents a group represented by the general formula (1-2):

wherein R$^a$ and R$^b$ independently represent a linear or branched alkyl group having 1 to 5 carbon atoms;

Y represents a group represented by the above general formula (1-2), or a linear or branched alkyl group having 1 to 8 carbon atoms;

Z represents a hydrogen atom, or an alkyl group having 1 to 4 carbon atoms; and

L represents an unsaturated hydrocarbon compound having at least two double bonds.

[2] The organoruthenium complex as described in [1], wherein the unsaturated hydrocarbon compound having at least two double bonds is 1,5-hexadiene, 1,5-cyclooctadiene, norbornadiene, 4-vinyl-1-cyclohexene or 1,3-pentadiene.

[3] A method for producing a ruthenium-containing thin film by a chemical vapor deposition method, wherein the organoruthenium complex as described in [1] or a solvent solution thereof is used as a ruthenium source.

[4] A method for producing a ruthenium-containing thin film by a chemical vapor deposition method, wherein the organoruthenium complex as described in [1] or a solvent solution thereof, and a hydrogen source are used.

[5] The method for producing a ruthenium-containing thin film as described in [4], wherein the hydrogen source is a hydrogen gas.

[6] A method for producing a ruthenium-containing thin film by a chemical vapor deposition method, wherein the organoruthenium complex as described in [1] or a solvent solution thereof, and an oxygen source are used.

[7] The method for producing a ruthenium-containing thin film as described in [6], wherein the oxygen source is an oxygen gas.

[8] The method for producing a ruthenium-containing thin film as described in [6], wherein the ruthenium-containing thin film produced is a metallic ruthenium film which contains substantially no oxygen atom.

[9] The method for producing a ruthenium-containing thin film by a chemical vapor deposition method as described in any one of [3] to [8], wherein the solvent used is at least one selected from the group consisting of aliphatic hydrocarbons, aromatic hydrocarbons, and ethers.

[10] Bis(acetylacetonato)(1,5-hexadiene)ruthenium represented by the formula (2-1):

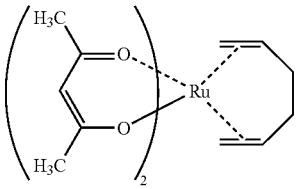

(2-1)

[11] Bis(acetylacetonato)(1,5-hexadiene)ruthenium as described in [10], wherein the complex is a ruthenium complex for producing a metallic ruthenium-containing thin film by a chemical vapor deposition method.

[12] A method for producing a ruthenium-containing thin film by a chemical vapor deposition method, wherein bis(acetylacetonato)(1,5-hexadiene)ruthenium as described in [10] or a solvent solution thereof is used as a ruthenium source.

[13] A method for producing a ruthenium-containing thin film by a chemical vapor deposition method, wherein bis(acetylacetonato)(1,5-hexadiene)ruthenium as described in [10] or a solvent solution thereof, and a hydrogen source are used.

[14] The method for producing a ruthenium-containing thin film as described in [13], wherein the hydrogen source is a hydrogen gas.

[15] A method for producing a ruthenium-containing thin film by a chemical vapor deposition method, wherein bis(acetylacetonato)(1,5-hexadiene)ruthenium as described in [10] or a solvent solution thereof, and an oxygen source are used.

[16] The method for producing a ruthenium-containing thin film as described in [15], wherein the oxygen source is an oxygen gas.

[17] The method for producing a ruthenium-containing thin film as described in [15], wherein the ruthenium-containing thin film produced is a metallic ruthenium film which contains substantially no oxygen atom.

[18] The method for producing a ruthenium-containing thin film by a chemical vapor deposition method as described in any one of [12] to [17], wherein the solvent used is at least one selected from the group consisting of aliphatic hydrocarbons, aromatic hydrocarbons, and ethers.

[19] Bis(acetylacetonato)(1,3-pentadiene)ruthenium represented by the formula (3-1):

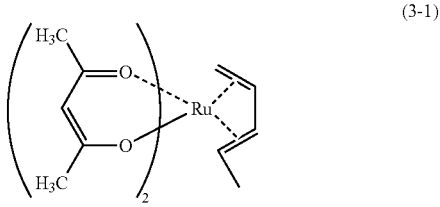

(3-1)

[20] Bis(acetylacetonato)(1,3-pentadiene)ruthenium as described in [19], wherein the complex is a ruthenium complex for producing a metallic ruthenium-containing thin film by a chemical vapor deposition method.

[21] A method for producing a ruthenium-containing thin film by a chemical vapor deposition method, wherein bis(acetylacetonato)(1,3-pentadiene)ruthenium as described in [19] or a solvent solution thereof is used as a ruthenium source.

[22] A method for producing a ruthenium-containing thin film by a chemical vapor deposition method, wherein bis(acetylacetonato)(1,3-pentadiene)ruthenium as described in [19] or a solvent solution thereof, and a hydrogen source are used.

[23] The method for producing a ruthenium-containing thin film as described in [22], wherein the hydrogen source is a hydrogen gas.

[24] A method for producing a ruthenium-containing thin film by a chemical vapor deposition method, wherein bis(acetylacetonato)(1,3-pentadiene)ruthenium as described in [19] or a solvent solution thereof, and an oxygen source are used.

[25] The method for producing a ruthenium-containing thin film as described in [24], wherein the oxygen source is an oxygen gas.

[26] The method for producing a ruthenium-containing thin film by a chemical vapor deposition method as described in any one of [21] to [25], wherein the solvent used is at least one selected from the group consisting of aliphatic hydrocarbons, aromatic hydrocarbons, and ethers.

[27] A method for producing a metallic ruthenium-containing thin film by a chemical vapor deposition method, wherein a ruthenium source and a hydrogen source are used, and the ruthenium source is an organoruthenium complex comprising a β-diketonato and an unsaturated hydrocarbon compound having at least two double bonds as a ligand, and represented by the general formula (4-1):

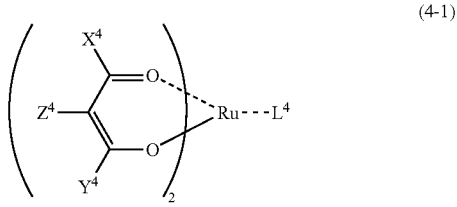

(4-1)

wherein $X^4$ and $Y^4$ independently represent a linear or branched alkyl group (with the proviso that the sum total of the carbon atoms in the groups represented by $X^4$ and $Y^4$ is 2 to 10);

$Z^4$ represents a hydrogen atom, or an alkyl group having 1 to 4 carbon atoms; and $L^4$ represents an unsaturated hydrocarbon compound having at least two double bonds, or a solvent solution thereof.

[28] The method for producing a metallic ruthenium-containing thin film by a chemical vapor deposition method as described in [27], wherein the unsaturated hydrocarbon compound having at least two double bonds is 1,5-hexadiene, 1,5-cyclooctadiene, norbornadiene, 4-vinyl-1-cyclohexene or 1,3-pentadiene.

[29] The method for producing a metallic ruthenium-containing thin film by a chemical vapor deposition method as described in [27], wherein the hydrogen source is a hydrogen gas.

[30] A method for producing a ruthenium-containing thin film by a chemical vapor deposition method, wherein a ruthenium source and an oxygen source are used, and the ruthenium source is an organoruthenium complex comprising a β-diketonato and an unsaturated hydrocarbon compound having at least two double bonds as a ligand, and represented by the above general formula (4-1), or a solvent solution thereof.

[31] The method for producing a ruthenium-containing thin film as described in [30], wherein the oxygen source is an oxygen gas.

[32] The method for producing a ruthenium-containing thin film by a chemical vapor deposition method as described in any one of [27] to [31], wherein the solvent used is at least one selected from the group consisting of aliphatic hydrocarbons, aromatic hydrocarbons, and ethers.

Effect of the Invention

According to the present invention, there can be provided an organoruthenium complex which has a low melting point, excellent stability against moisture, air and heat, and is suitable for the film formation by a CVD method (an organoruthenium complex represented by the above general formula (1-1)). There can be also provided a method for producing a ruthenium-containing thin film using the organoruthenium complex. Furthermore, there can be provided a method for producing a metallic ruthenium-containing thin film which does not comprise a ruthenium oxide, using the organoruthenium complex, by a chemical vapor deposition method.

In addition, according to the present invention, there can be provided bis(acetylacetonato)(1,5-hexadiene)ruthenium and bis(acetylacetonato)(1,3-pentadiene)ruthenium. There can be also provided a method for producing a metallic ruthenium-containing thin film which does not comprise a ruthenium oxide, using at least one of these ruthenium complexes, by a chemical vapor deposition method.

Furthermore, according to the present invention, there can be provided a method for producing a metallic ruthenium-containing thin film which does not comprise a ruthenium oxide, using an organoruthenium complex comprising a β-diketonato and an unsaturated hydrocarbon compound having at least two double bonds as a ligand other than the above-mentioned organoruthenium complexes, by a chemical vapor deposition method.

BRIEF DESCRIPTION OF THE DRAWINGS

FIG. 1 is a diagram illustrating the construction of the vapor deposition apparatus.

DESCRIPTION OF THE MAIN SYMBOLS

1A: mass flow controller,
1B: mass flow controller,
2: stop valve,
3: vaporizer,
4: reactor,
5: pressure gage,
6: valve,
7: trap,
10A: pre-heater,
10B: heater for vaporizer,
10C: heater for reactor,
20: organoruthenium complex melt as a raw material,
21: substrate.

BEST MODE FOR CARRYING OUT THE INVENTION

First Embodiment of the Present Invention

There will be described the first embodiment of the present invention, i.e. an organoruthenium complex represented by the above general formula (1-1) which comprises a β-diketonato having an alkoxyalkylmethyl group and an unsaturated hydrocarbon compound having at least two double bonds as a ligand, and a method for producing a ruthenium-containing thin film using the ruthenium complex. The organoruthenium complex has a low melting point, excellent stability against moisture, air and heat, and is suitable for the film formation by a CVD method. Furthermore, a metallic ruthenium-containing thin film which does not comprise a ruthenium oxide can be produced by a chemical vapor deposition method using the organoruthenium complex as a ruthenium source.

The organoruthenium complex of the present invention comprises a β-diketonato having an alkoxyalkylmethyl group and an unsaturated hydrocarbon compound having at least two double bonds as a ligand, and is represented by the above general formula (1-1). In the general formula (1-1), X represents an alkoxyalkylmethyl group represented by the above general formula (1-2) in which $R^a$ and $R^b$ independently represent a linear or branched alkyl group having 1 to 5 carbon atoms such as methyl, ethyl, n-propyl, isopropyl, n-butyl, isobutyl, t-butyl, and pentyl. Y represents a group represented by the above general formula (1-2), or a linear or branched alkyl group having 1 to 8 carbon atoms such as methyl, ethyl, n-propyl, isopropyl, n-butyl, isobutyl, t-butyl, pentyl, hexyl, heptyl, and octyl. Z represents a hydrogen atom, or a linear or branched alkyl group having 1 to 4 carbon atoms such as methyl, ethyl, n-propyl, isopropyl, n-butyl, isobutyl, and t-butyl. $R^a$ and $R^b$ are preferably methyl or ethyl, more preferably methyl. Y is preferably a linear or branched alkyl group having 1 to 3 carbon atoms, more preferably isopropyl. Z is preferably a hydrogen atom. L represents an unsaturated hydrocarbon compound having at least two double bonds. L is preferably 1,5-hexadiene, 1,5-cyclooctadiene, norbornadiene, 1,4-cyclohexadiene, 2,5-dimethyl-2,4-hexadiene, 4-vinyl-1-cyclohexene, or 1,3-pentadiene, for example.

β-diketone from which the β-diketonato ligand in the organoruthenium complex of the present invention is derived may be easily prepared by a known method. The method will be described in Reference Examples below. The organoruthenium complex of the present invention may be prepared by reference to the known method for preparing a β-diketonato ruthenium complex having a diene compound as a ligand. For example, the organoruthenium complex of the present invention may be prepared by reacting a ruthenium compound such as ruthenium chloride with a diene compound in an organic solvent, and then adding a β-diketone compound thereto and reacting them.

Specific examples of the organoruthenium complex of the present invention which comprises a β-diketonato having an alkoxyalkylmethyl group and an unsaturated hydrocarbon compound having at least two double bonds as a ligand include the complexes represented by the following formulas (1-3) to (1-9).

(1-3)

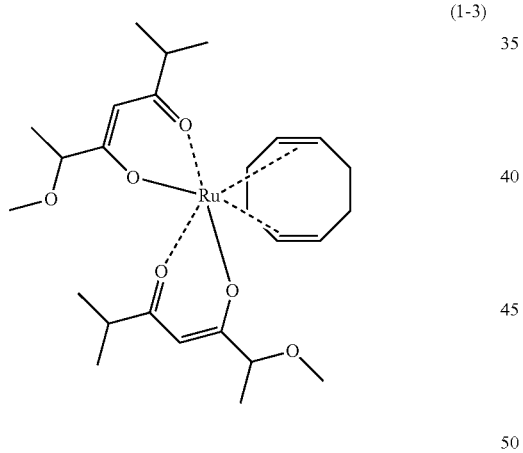

(1-4)

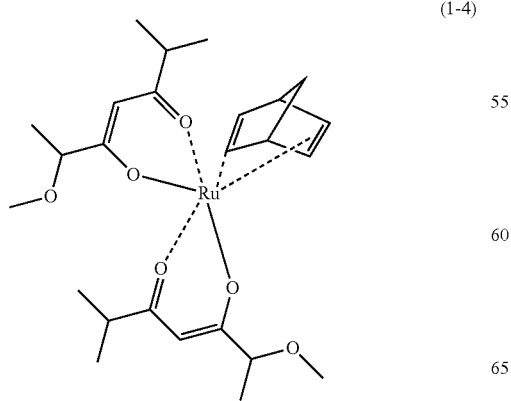

-continued (1-5)

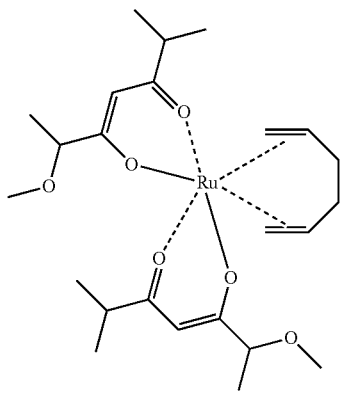

(1-6)

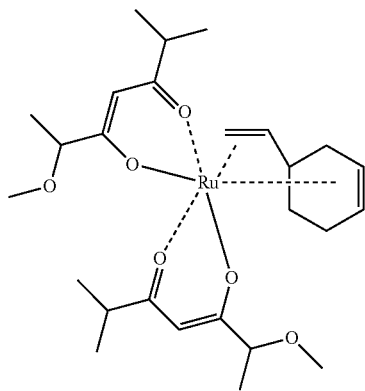

(1-7)

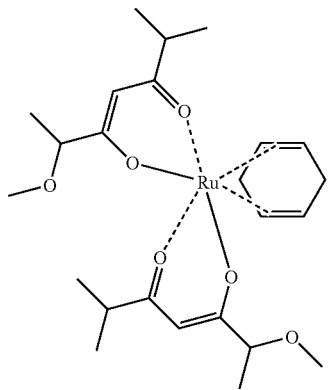

(1-8)

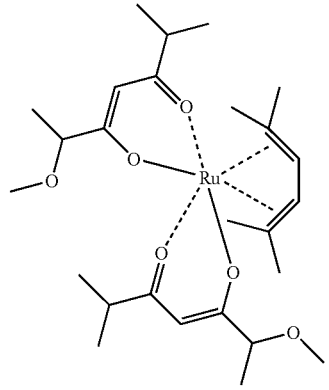

-continued (1-9)

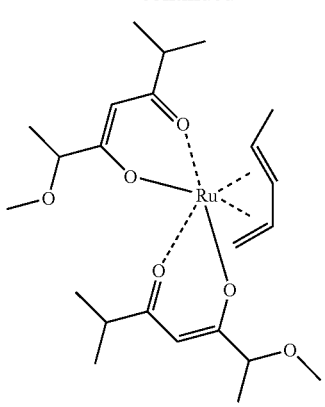

In the CVD method of the present invention, it is necessary to vaporize the organoruthenium complex for the formation of a thin film. The organoruthenium complex of the present invention may be filled or fed into a vaporizing chamber, and then vaporized therein, for example. Alternatively, a solution prepared by diluting the organoruthenium complex with a suitable solvent (an aliphatic hydrocarbon such as hexane, methylcyclohexane, ethylcyclohexane and octane; an aromatic hydrocarbon such as toluene; or an ether such as tetrahydrofuran and dibutyl ether, for example) may be fed into a vaporizing chamber with a liquid feed pump, and then vaporized therein (a solution method).

The metal may be vapor-deposited on a substrate by a known CVD method. For example, the organoruthenium complex, together with a hydrogen source (a reducing gas such as a hydrogen gas, or an alcohol, for example) or an oxidizing gas such as an oxygen gas, may be supplied onto a heated substrate under atmospheric or reduced pressure to vapor-deposit a metallic ruthenium film on the substrate. Alternatively, a metallic ruthenium film may be vapor-deposited on a substrate by the thermal decomposition of the organoruthenium complex. A metallic ruthenium film may be also vapor-deposited on a substrate by a plasma CVD method. When using the organoruthenium complex represented by the general formula (1-1) as a ruthenium source, a metallic ruthenium film which contains substantially no oxygen atom, i.e. a metallic ruthenium film which does not comprise a ruthenium oxide, can be produced, even though an oxidizing gas such as an oxygen gas is used.

When using the organoruthenium complex, together with a hydrogen source or an oxygen gas, to vapor-deposit a metallic ruthenium film, the pressure in the reaction system is preferably 1 Pa to 200 kPa, more preferably 10 Pa to 110 kPa, and the temperature of the object on which a film is to be formed is preferably 150 to 500° C., more preferably 200 to 400° C. When using the organoruthenium complex, together with a hydrogen gas or an oxygen gas, to vapor-deposit a metallic thin film, the content of a hydrogen gas or an oxygen gas is preferably 0.01 to 95 vol %, more preferably 0.1 to 90 vol % based on the total amount of the gases.

Second Embodiment of the Present Invention

There will be described the second embodiment of the present invention, i.e. bis(acetylacetonato)(1,5-hexadiene) ruthenium represented by the above formula (2-1), and a method for producing a ruthenium-containing thin film using the ruthenium complex. A metallic ruthenium-containing thin film which does not comprise a ruthenium oxide can be produced by a chemical vapor deposition method using the ruthenium complex as a ruthenium source.

Bis(acetylacetonato)(1,5-hexadiene)ruthenium may be prepared by reference to the known method for preparing a β-diketonato ruthenium complex having a diene compound as a ligand. For example, bis(acetylacetonato)(1,5-hexadiene)ruthenium may be prepared by reacting a ruthenium compound such as ruthenium chloride with 1,5-hexadiene in an organic solvent, and then adding acetylacetone thereto and reacting them.

In the CVD method of the present invention, it is necessary to vaporize bis(acetylacetonato)(1,5-hexadiene)ruthenium (hereinafter, referred to as "the organoruthenium complex" or "the ruthenium complex") for the formation of a thin film. The organoruthenium complex of the present invention may be filled or fed into a vaporizing chamber, and then vaporized therein, for example. Alternatively, a solution prepared by diluting the organoruthenium complex with a suitable solvent (an aliphatic hydrocarbon such as hexane, methylcyclohexane, ethylcyclohexane and octane; an aromatic hydrocarbon such as toluene; or an ether such as tetrahydrofuran and dibutyl ether, for example) may be fed into a vaporizing chamber with a liquid feed pump, and then vaporized therein (a solution method).

The metal may be vapor-deposited on a substrate by a known CVD method. For example, the organoruthenium complex, together with a hydrogen source (a reducing gas such as a hydrogen gas, or an alcohol, for example) or an oxidizing gas such as an oxygen gas, may be supplied onto a heated substrate under atmospheric or reduced pressure to vapor-deposit a metallic ruthenium film on the substrate. Alternatively, a metallic ruthenium film may be vapor-deposited on a substrate by the thermal decomposition of the organoruthenium complex. A metallic ruthenium film may be also vapor-deposited on a substrate by a plasma CVD method. When using bis(acetylacetonato)(1,5-hexadiene)ruthenium represented by the formula (2-1) as a ruthenium source, a metallic ruthenium film which contains substantially no oxygen atom, i.e. a metallic ruthenium film which does not comprise a ruthenium oxide, can be produced, even though an oxidizing gas such as an oxygen gas is used.

When using the organoruthenium complex, together with a hydrogen source or an oxygen gas, to vapor-deposit a metallic ruthenium film, the pressure in the reaction system is preferably 1 Pa to 200 kPa, more preferably 10 Pa to 110 kPa, and the temperature of the object on which a film is to be formed is preferably 150 to 500° C., more preferably 200 to 400° C. When using the organoruthenium complex, together with a hydrogen gas or an oxygen gas, to vapor-deposit a metallic thin film, the content of a hydrogen gas or an oxygen gas is preferably 0.01 to 95 vol %, more preferably 0.1 to 90 vol % based on the total amount of the gases.

Third Embodiment of the Present Invention

There will be described the third embodiment of the present invention, i.e. bis(acetylacetonato)(1,3-pentadiene) ruthenium represented by the above formula (3-1), and a method for producing a ruthenium-containing thin film using the ruthenium complex. A metallic ruthenium-containing thin film which does not comprise a ruthenium oxide can be produced by a chemical vapor deposition method using the ruthenium complex as a ruthenium source.

Bis(acetylacetonato)(1,3-pentadiene)ruthenium may be prepared by reference to the known method for preparing a β-diketonato ruthenium complex having a diene compound as a ligand. For example, bis(acetylacetonato)(1,3-pentadiene)ruthenium may be prepared by reacting a ruthenium compound such as ruthenium chloride with 1,3-pentadiene in an organic solvent, and then adding acetylacetone thereto and reacting them.

In the CVD method of the present invention, it is necessary to vaporize bis(acetylacetonato)(1,3-pentadiene)ruthenium (hereinafter, referred to as "the organoruthenium complex" or "the ruthenium complex") for the formation of a thin film. The organoruthenium complex of the present invention may be filled or fed into a vaporizing chamber, and then vaporized therein, for example. Alternatively, a solution prepared by diluting the organoruthenium complex with a suitable solvent (an aliphatic hydrocarbon such as hexane, methylcyclohexane, ethylcyclohexane and octane; an aromatic hydrocarbon such as toluene; or an ether such as tetrahydrofuran and dibutyl ether, for example) may be fed into a vaporizing chamber with a liquid feed pump, and then vaporized therein (a solution method).

The metal may be vapor-deposited on a substrate by a known CVD method. For example, the organoruthenium complex, together with a hydrogen source (a reducing gas such as a hydrogen gas, or an alcohol, for example), may be supplied onto a heated substrate under atmospheric or reduced pressure to vapor-deposit a metallic ruthenium film on the substrate. Alternatively, only the organoruthenium complex may be supplied onto a heated substrate to vapor-deposit a metallic ruthenium film on the substrate. A metallic ruthenium film may be also vapor-deposited on a substrate by a plasma CVD method. The organoruthenium complex, together with an oxidizing gas such as an oxygen gas, may be supplied onto a heated substrate under atmospheric or reduced pressure to vapor-deposit a ruthenium-containing film on the substrate.

When using the organoruthenium complex to vapor-deposit a metallic ruthenium film, the pressure in the reaction system is preferably 1 Pa to 200 kPa, more preferably 10 Pa to 110 kPa, and the temperature of the object on which a film is to be formed is preferably 150 to 650° C., more preferably 200 to 550° C. When using the organoruthenium complex, together with a hydrogen gas, to vapor-deposit a metallic thin film, the content of a hydrogen gas is preferably 0.01 to 95 vol %, more preferably 0.1 to 90 vol % based on the total amount of the gases.

Fourth Embodiment of the Present Invention

There will be described the fourth embodiment of the present invention, i.e. a method for producing a metallic ruthenium-containing thin film by a chemical vapor deposition method using the organoruthenium complex represented by the above general formula (4-1) which comprises a 6-diketonato and an unsaturated hydrocarbon compound having at least two double bonds as a ligand, and a hydrogen source.

The organoruthenium complex of the present invention comprises a β-diketonato and an unsaturated hydrocarbon compound having at least two double bonds as a ligand, and is represented by the above general formula (4-1). In the general formula (4-1), $X^4$ and $Y^4$ independently represent a linear or branched alkyl group such as methyl, ethyl, n-propyl, isopropyl, n-butyl, isobutyl, t-butyl, pentyl, isopentyl, neopentyl, n-hexyl, and isohexyl. The sum total of the carbon atoms in the groups represented by $X^4$ and $Y^4$ is 2 to 10, preferably 3 to 10. $Z^4$ represents a hydrogen atom, or a linear or branched alkyl group having 1 to 4 carbon atoms such as methyl, ethyl, n-propyl, isopropyl, n-butyl, isobutyl, and t-butyl. $L^4$ represents an unsaturated hydrocarbon compound having at least two double bonds. $L^4$ is preferably 1,5-hexadiene, 1,5-cyclooctadiene, norbornadiene, 1,4-cyclohexadiene, 2,5-dimethyl-2,4-hexadiene, 4-vinyl-1-cyclohexene, or 1,3-pentadiene, for example.

β-diketone from which the β-diketonato ligand in the organoruthenium complex of the present invention is derived may be easily prepared by a known method.

Specific examples of the organoruthenium complex of the present invention which comprises a β-diketonato and an unsaturated hydrocarbon compound having at least two double bonds as a ligand include the complexes represented by the following formulas (4-2) to (4-29).

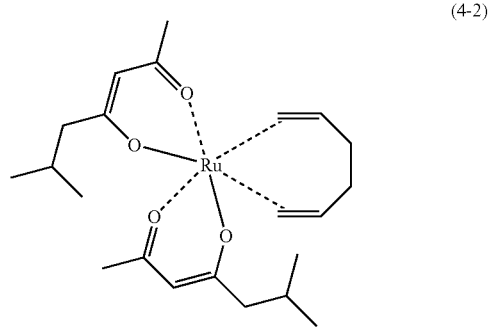

(4-2)

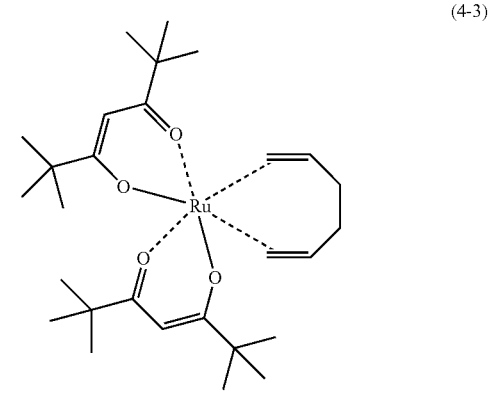

(4-3)

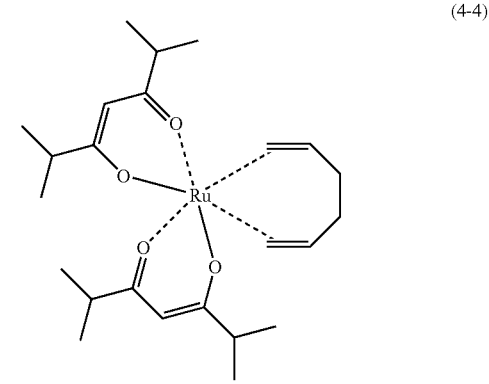

(4-4)

(4-5)
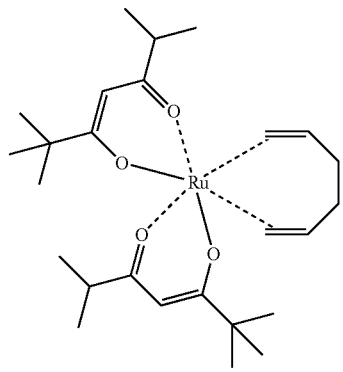
(4-6)
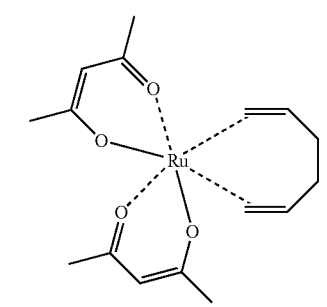
(4-7)
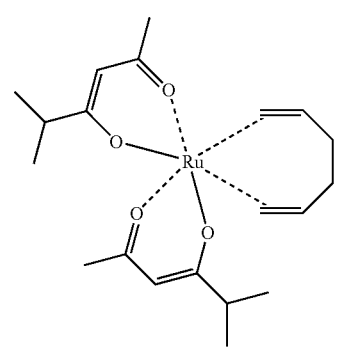
(4-8)
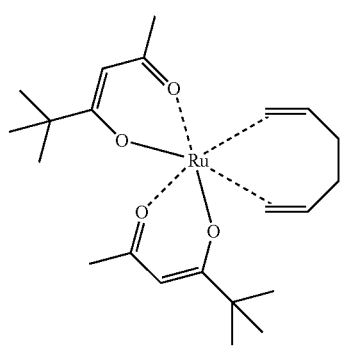
(4-9)
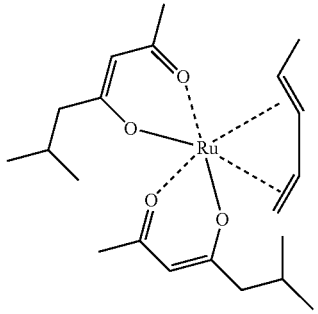
(4-10)
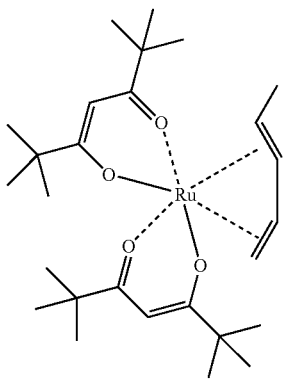
(4-11)
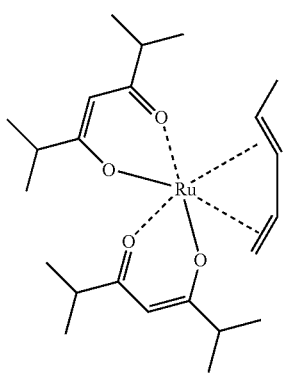
(4-12)
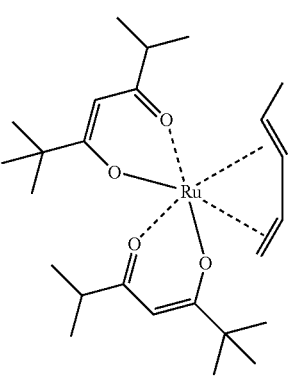

(4-13)
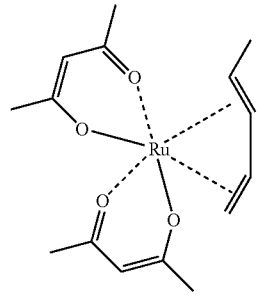
(4-14)
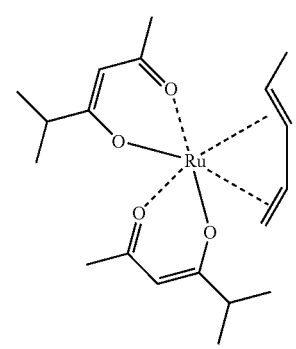
(4-15)
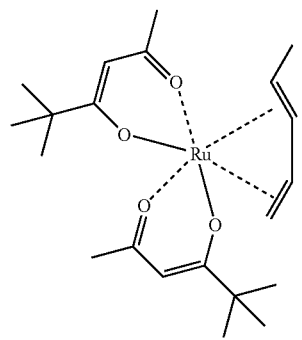
(4-16)
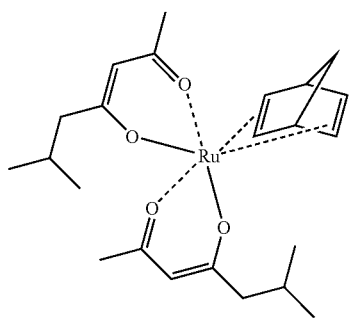
(4-17)
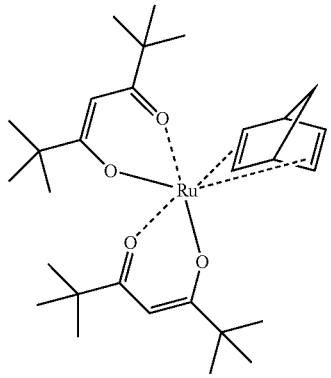
(4-18)
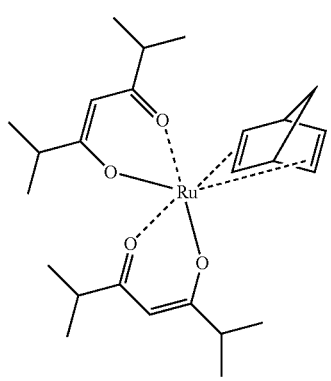
(4-19)
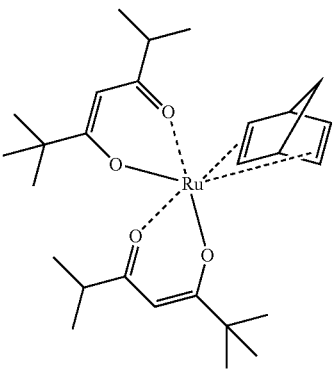
(4-20)
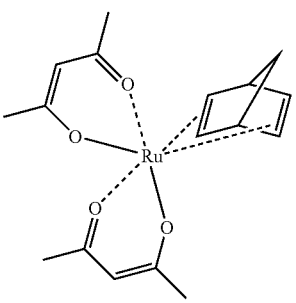

(4-21)
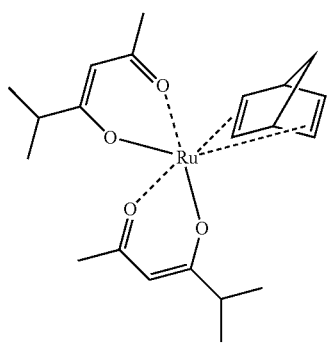
(4-22)
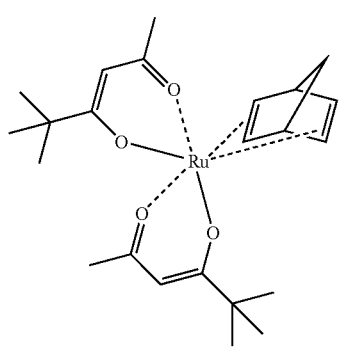
(4-23)
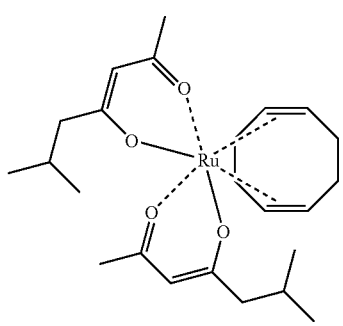
(4-24)
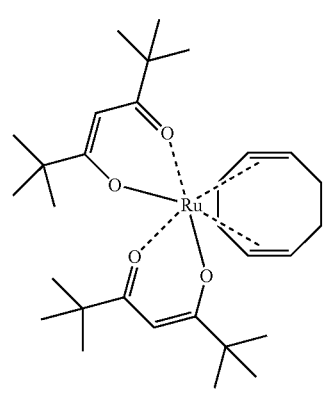
(4-25)
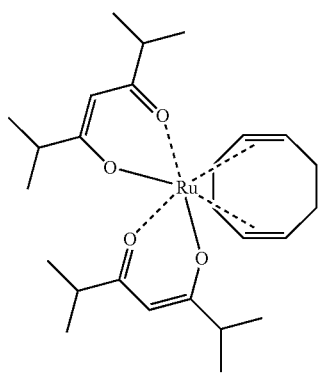
(4-26)
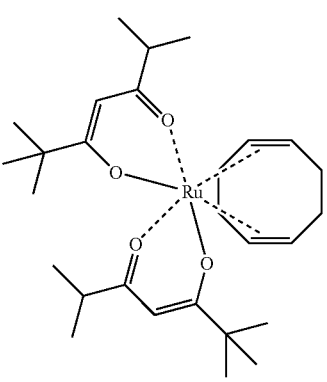
(4-27)
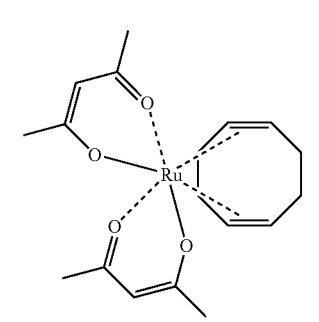
(4-28)
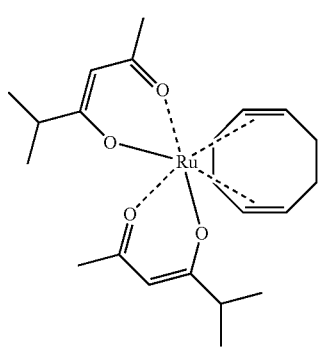

(4-29)

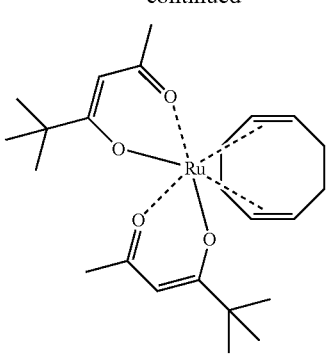

In the CVD method, it is necessary to vaporize the organoruthenium complex for the formation of a thin film. The organoruthenium complex of the present invention may be filled or fed into a vaporizing chamber, and then vaporized therein, for example. Alternatively, a solution prepared by diluting the organoruthenium complex with a suitable solvent (an aliphatic hydrocarbon such as hexane, methylcyclohexane, ethylcyclohexane and octane; an aromatic hydrocarbon such as toluene; or an ether such as tetrahydrofuran and dibutyl ether, for example) may be fed into a vaporizing chamber with a liquid feed pump, and then vaporized therein (a solution method).

The metal may be vapor-deposited on a substrate by a known CVD method. For example, the organoruthenium complex, together with a hydrogen source (a reducing gas such as a hydrogen gas, or an alcohol, for example), may be supplied onto a heated substrate under atmospheric or reduced pressure to vapor-deposit a metallic ruthenium film on the substrate. A metallic ruthenium film may be also vapor-deposited on a substrate by a plasma CVD method. The organoruthenium complex, together with an oxidizing gas such as an oxygen gas, may be supplied onto a heated substrate under atmospheric or reduced pressure to vapor-deposit a ruthenium-containing film on the substrate.

When using the organoruthenium complex, together with a hydrogen source, to vapor-deposit a metallic ruthenium film, the pressure in the reaction system is preferably 1 Pa to 200 kPa, more preferably 10 Pa to 110 kPa, and the temperature of the object on which a film is to be formed is preferably 150 to 500° C., more preferably 200 to 400° C. When using the organoruthenium complex, together with a hydrogen gas, to vapor-deposit a metallic thin film, the content of a hydrogen gas is preferably 0.01 to 95 vol %, more preferably 0.1 to 90 vol % based on the total amount of the gases.

EXAMPLES

The present invention is more specifically described below with reference to the Examples. However, the present invention is not restricted to these Examples.

Reference Example 1-1

Preparation of 2-methoxy-6-methyl-3,5-heptanedione (Hereinafter, Referred to as "mopd")

In a 200 mL-volume flask equipped with a stirrer, a thermometer and a dropping funnel was placed 5.16 g (132 mmol) of sodium amide. After the inside of the reaction system (the flask) was replaced with argon, 80 mL of toluene was added. And then, while cooling the flask with water, 12.0 g (139.3 mmol) of 3-methyl-2-butanone was slowly dropped into the flask, and the resulting mixture was stirred for 15 minutes. Subsequently, 5.65 g (47.8 mmol) of methyl 2-methoxy propionate which was prepared in the same way as Reference Example 1-1 was dropped into the flask, and the resulting mixture was reacted while stirring for 30 minutes. After the completion of the reaction, 50 mL of water was added to the resulting mixture while cooling the flask with ice, and the water layer was separated and neutralized with acetic acid. The water layer was extracted with ether, and the ether extract was washed with water and dried with anhydrous sodium sulfate. After the filtration of the ether extract, the filtrate was concentrated, and the concentrate was distilled under reduced pressure (41° C., 27 Pa), to give 4.25 g of 2-methoxy-6-methyl-3,5-heptanedione as a colorless liquid (isolation yield: 52%).

The obtained 2-methoxy-6-methyl-3,5-heptanedione had the following properties:
$^1$H-NMR (CDCl$_3$, δ (ppm)): 1.17 (6H, d), 1.30 (0.15H, d), 1.36 (2.85H, d), 2.48-2.57 (0.95H, m), 2.59-2.73 (0.05H, m), 3.36 (0.15H, s), 3.37 (2.85H, s), 3.71-3.78 (1H, m), 3.78 (0.1H, s), 5.81 (0.95H, s), 15.4 (0.95H, s).
IR (neat (cm$^{-1}$)): 2976, 2936, 1607 (br), 1462, 1366, 1328, 1210, 1120, 910, 805.
(The peak at 1607 cm$^{-1}$ is a peak characteristic of δ-diketone.)
MS (m/e): 142, 113, 59, 43.

Example 1-1

Preparation of bis(2-methoxy-6-methyl-3,5-heptanedionato)(1,5-cyclooctadiene)ruthenium(II) (Hereinafter, Referred to as "[Ru(mopd)$_2$ (cod)]")

In a 100 mL-volume flask equipped with a stirrer, a thermometer and a dropping funnel were placed 3.61 g (13.8 mmol) of ruthenium trichloride trihydrate, 2.96 g (27.3 mmol) of 1,5-cyclooctadiene, and 25 mL of isopropyl alcohol. And then, the resulting mixture was refluxed while stirring for 3 hours. Subsequently, an aqueous solution comprising 7.17 g (41.6 mmol) of 2-methoxy-6-methyl-3,5-heptanedione and 1.67 g (41.8 mmol) of sodium hydroxide was dropped into the flask, and the resulting mixture was reacted while stirring for 0.5 hours. After the completion of the reaction, 40 mL of methylcyclohexane and 30 mL of water were added to the resulting mixture, and the organic layer was separated and dried with anhydrous sodium sulfate. After the filtration of the organic layer, the filtrate was concentrated, and the concentrate was distilled under reduced pressure (190° C., 49 Pa), to give a yellow-brown viscous liquid. The obtained liquid was purified with silica gel column chromatography (developing solvent: hexane/ethyl acetate=9/1 (volume ratio)), to give 4.57 g of bis(2-methoxy-6-methyl-3,5-heptanedionato)(1,5-cyclooctadiene)ruthenium(II) as a yellow-brown viscous liquid (isolation yield: 60%).

The obtained bis(2-methoxy-6-methyl-3,5-heptanedionato)(1,5-cyclooctadiene)ruthenium(II) is a novel compound and had the following properties:
IR (neat (cm$^{-1}$)): 2971, 2929, 2871, 2821, 1592, 1570, 1522, 1439, 1426, 1363, 1331, 1211, 1156, 1119, 1060, 915, 869, 793, 576.
(The peak characteristic of β-diketone (1607 cm$^{-1}$) disappeared and the peak characteristic of β-diketonato (1570 cm$^{-1}$) was observed.)

Elemental Analysis ($C_{26}H_{42}O_6Ru$): carbon: 56.9%, hydrogen: 7.78%, ruthenium: 18.1%.
(Theoretical value: carbon: 56.6%, hydrogen: 7.67%, ruthenium: 18.3%)
MS (m/e): 552, 444, 59.

Example 1-2

Preparation of bis(2-methoxy-6-methyl-3,5-heptanedionato)(norbornadiene)ruthenium(II) (Hereinafter, Referred to as "[Ru(mopd)$_2$ (nbd)]")

The reaction was conducted in the same way as Example 1-1, except that 2.51 g (27.3 mmol) of norbornadiene was used instead of 1,5-cyclooctadiene, to give 3.85 g of bis(2-methoxy-6-methyl-3,5-heptanedionato)(norbornadiene)ruthenium(II) as a yellow-brown viscous liquid (isolation yield: 52%).
The obtained bis(2-methoxy-6-methyl-3,5-heptanedionato)(norbornadiene)ruthenium(II) is a novel compound and had the following properties:
IR (neat (cm$^{-1}$)): 2972, 2930, 2872, 2821, 1592, 1571, 1522, 1433, 1363, 1330, 1211, 1154, 1120, 1060, 1011, 915, 869, 794, 577.
(The peak characteristic of β-diketone (1607 cm$^{-1}$) disappeared and the peak characteristic of β-diketonato (1571 cm$^{-1}$) was observed.)
Elemental Analysis ($C_{25}H_{38}O_6Ru$): carbon: 56.4%, hydrogen: 7.22%, ruthenium: 18.8%.
(Theoretical value: carbon: 56.1%, hydrogen: 7.15%, ruthenium: 18.9%)
MS (m/e): 536, 444, 193, 59.

Example 1-3

Preparation of bis(2-methoxy-6-methyl-3,5-heptanedionato)(1,5-hexadiene)ruthenium(II) (Hereinafter, Referred to as "[Ru(mopd)$_2$ (hd)]")

The reaction was conducted in the same way as Example 1-1, except that 2.24 g (27.3 mmol) of 1,5-hexadiene was used instead of 1,5-cyclooctadiene, to give 3.05 g of bis(2-methoxy-6-methyl-3,5-heptanedionato)(1,5-hexadiene)ruthenium(II) as a yellow-brown viscous liquid (isolation yield: 42%).
The obtained bis(2-methoxy-6-methyl-3,5-heptanedionato)(1,5-hexadiene)ruthenium(II) is a novel compound and had the following properties:
IR (neat (cm$^{-1}$)): 2972, 2931, 2872, 2822, 1566, 1524, 1429, 1365, 1331, 1211, 1156, 1120, 1060, 968, 915, 870, 799, 611, 579.
(The peak characteristic of β-diketone (1607 cm$^{-1}$) disappeared and the peak characteristic of β-diketonato (1566 cm$^{-1}$) was observed.)
Elemental Analysis ($C_{24}H_{40}O_6Ru$): carbon: 56.4%, hydrogen: 7.22%, ruthenium: 18.8%.
(Theoretical value: carbon: 54.8%, hydrogen: 7.67%, ruthenium: 19.2%)
MS (m/e): 526, 444, 59.

Example 1-4

Preparation of bis(2-methoxy-6-methyl-3,5-heptanedionato)(4-vinyl-1-cyclohexene)ruthenium(II) (Hereinafter, Referred to as "[Ru(mopd)$_2$ (vch)]")

The reaction was conducted in the same way as Example 1-1, except that 2.95 g (27.3 mmol) of 4-vinyl-1-cyclohexene was used instead of 1,5-cyclooctadiene, to give 4.27 g of bis(2-methoxy-6-methyl-3,5-heptanedionato)(4-vinyl-1-cyclohexene)ruthenium(II) as a yellow-brown viscous liquid (isolation yield: 56%).
The obtained bis(2-methoxy-6-methyl-3,5-heptanedionato)(4-vinyl-1-cyclohexene)ruthenium(II) is a novel compound and had the following properties:
IR (neat (cm$^{-1}$)): 2973, 2932, 2874, 2822, 1568, 1524, 1429, 1363, 1332, 1211, 1156, 1120, 1060, 915, 798, 580.
(The peak characteristic of β-diketone (1607 cm$^{-1}$) disappeared and the peak characteristic of β-diketonato (1568 cm$^{-1}$) was observed.)
Elemental Analysis ($C_{26}H_{42}O_6Ru$): carbon: 56.9%, hydrogen: 7.73%, ruthenium: 18.2%.
(Theoretical value: carbon: 56.6%, hydrogen: 7.67%, ruthenium: 18.3%)
MS (m/e): 552, 444, 113, 59.

Example 1-5

Preparation of bis(2-methoxy-6-methyl-3,5-heptanedionato)(1,3-pentadiene)ruthenium(II) (Hereinafter, Referred to as "[Ru(mopd)$_2$ (pd)]")

The reaction was conducted in the same way as Example 1-1, except that 1.86 g (27.3 mmol) of 1,3-pentadiene was used instead of 1,5-cyclooctadiene, to give 2.68 g of bis(2-methoxy-6-methyl-3,5-heptanedionato)(1,3-pentadiene)ruthenium(II) as a yellow-brown viscous liquid (isolation yield: 38%).
The obtained bis(2-methoxy-6-methyl-3,5-heptanedionato)(1,3-pentadiene)ruthenium(II) is a novel compound and had the following properties:
IR (neat (cm$^{-1}$)): 2973, 2931, 2873, 2822, 1564, 1524, 1428, 1367, 1331, 1211, 1156, 1120, 1060, 966, 916, 800, 580.
(The peak characteristic of β-diketone (1607 cm$^{-1}$) disappeared and the peak characteristic of β-diketonato (1564 cm$^{-1}$) was observed.)
Elemental Analysis ($C_{23}H_{38}O_6Ru$): carbon: 54.5%, hydrogen: 7.51%, ruthenium: 19.6%.
(Theoretical value: carbon: 54.0%, hydrogen: 7.49%, ruthenium: 19.8%)
MS (m/e): 512, 444, 59.

Examples 1-6-1-12

Vapor-Deposition Test

Formation of Ruthenium Thin Film

The vapor-deposition tests were conducted on the organoruthenium complexes obtained in Examples 1-1-1-5 ([Ru(mopd)$_2$ (cod)], [Ru(mopd)$_2$ (nbd)], [Ru(mopd)$_2$ (hd)], [Ru(mopd)$_2$ (vch)], and [Ru(mopd)$_2$ (pd)]) by the CVD method to evaluate the film-forming properties.
The apparatus shown in FIG. 1 was used to conduct the evaluation tests. The ruthenium complex 20 in a vaporizer (glass ampule) 3 is heated and vaporized by a heater 10B. The vaporized ruthenium complex 20 is discharged from the vaporizer 3, together with a helium gas which is fed into the vaporizer 3 via a mass flow controller 1A after pre-heating by a pre-heater 10A. The gas discharged from the vaporizer 3 is fed into a reactor 4, together with a hydrogen gas (Examples 1-6-1-10) or an oxygen gas (Example 1-11) which is fed via a mass flow controller 1B and a stop valve 2. In Example 1-12, the valve 2 is closed, and neither a hydrogen gas nor an oxygen gas is fed into the reactor 4. The pressure in the reaction system (the reactor) is controlled to a predetermined pressure by opening and closing a valve 6 arranged upstream of a vacuum pump, and is monitored by a pressure gage 5. The central part of the glass reactor can be heated by a heater 10C. The ruthenium complex introduced into the reactor is reduced on the surface of the substrate 21 which is disposed in the central part of the reactor and heated to a predetermined temperature by the heater 10C, thereby depositing a metallic ruthenium thin film on the substrate 21. The gas discharged from the reactor 4 is exhausted to the atmosphere via a trap 7 and the vacuum pump.

The vapor-deposition conditions and results (film properties) are shown in Table 1 and Table 2. The rectangular substrate of 7 mm×40 mm was used as the substrate on which the film was to be vapor-deposited.

TABLE 1

|   | Vapor-deposition conditions | Film properties |
| --- | --- | --- |
| Example 1-6 | Ru complex: [Ru(mopd)$_2$(cod)]<br>Ru complex vaporization temp.: 165° C.<br>He carrier gas flow rate: 30 ml/min.<br>Hydrogen flow rate: 120 ml/min.<br>Substrate material: SiO$_2$/Si<br>Substrate temp.: 300° C.<br>Pressure in the reactor: 7980 Pa<br>Vapor-deposition time: 30 min. | Film thickness:<br>15 nm<br>XPS analysis:<br>Metallic ruthenium<br>film |
| Example 1-7 | Ru complex: [Ru(mopd)$_2$(nbd)]<br>Ru complex vaporization temp.: 150° C.<br>He carrier gas flow rate: 30 ml/min.<br>Hydrogen flow rate: 120 ml/min.<br>Substrate material: SiO$_2$/Si<br>Substrate temp.: 300° C.<br>Pressure in the reactor: 7980 Pa<br>Vapor-deposition time: 30 min. | Film thickness:<br>15 nm<br>XPS analysis:<br>Metallic ruthenium<br>film |
| Example 1-8 | Ru complex: [Ru(mopd)$_2$(hd)]<br>Ru complex vaporization temp.: 165° C.<br>He carrier gas flow rate: 30 ml/min.<br>Hydrogen flow rate: 120 ml/min.<br>Substrate material: SiO$_2$/Si<br>Substrate temp.: 270° C.<br>Pressure in the reactor: 7980 Pa<br>Vapor-deposition time: 30 min. | Film thickness:<br>10 nm<br>XPS analysis:<br>Metallic ruthenium<br>film |
| Example 1-9 | Ru complex: [Ru(mopd)$_2$(vch)]<br>Ru complex vaporization temp.: 165° C.<br>He carrier gas flow rate: 30 ml/min.<br>Hydrogen flow rate: 120 ml/min.<br>Substrate material: SiO$_2$/Si<br>Substrate temp.: 300° C.<br>Pressure in the reactor: 7980 Pa<br>Vapor-deposition time: 30 min. | Film thickness:<br>15 nm<br>XPS analysis:<br>Metallic ruthenium<br>film |

TABLE 2

|   | Vapor-deposition conditions | Film properties |
| --- | --- | --- |
| Example 1-10 | Ru complex: [Ru(mopd)$_2$(pd)]<br>Ru complex vaporization temp.: 165° C.<br>He carrier gas flow rate: 30 ml/min.<br>Hydrogen flow rate: 120 ml/min.<br>Substrate material: SiO$_2$/Si<br>Substrate temp.: 270° C.<br>Pressure in the reactor: 7980 Pa<br>Vapor-deposition time: 30 min. | Film thickness:<br>10 nm<br>XPS analysis:<br>Metallic ruthenium<br>film |
| Example 1-11 | Ru complex: [Ru(mopd)$_2$(hd)]<br>Ru complex vaporization temp.: 130° C.<br>He carrier gas flow rate: 40 ml/min.<br>Oxygen flow rate: 5 ml/min.<br>Substrate material: SiO$_2$/Si<br>Substrate temp.: 300° C.<br>Pressure in the reactor: 718 Pa<br>Vapor-deposition time: 10 min. | Film thickness:<br>350 nm<br>XPS analysis:<br>Metallic ruthenium<br>film |
| Example 1-12 | Ru complex: [Ru(mopd)$_2$(hd)]<br>Ru complex vaporization temp.: 130° C.<br>He carrier gas flow rate: 40 ml/min.<br>Substrate material: SiO$_2$/Si<br>Substrate temp.: 300° C.<br>Pressure in the reactor: 718 Pa<br>Vapor-deposition time: 2 min. | Film thickness:<br>5 nm<br>XPS analysis:<br>Metallic ruthenium<br>film |

The results indicate that the organoruthenium complexes of the present invention ([Ru(mopd)$_2$ (cod)], [Ru(mopd)$_2$ (nbd)], [Ru(mopd)$_2$ (hd)], [Ru(mopd)$_2$ (vch)], and [Ru (mopd)$_2$ (pd)]) have the excellent metallic ruthenium film-forming properties at a low temperature under any conditions.

Example 2-1

Preparation of bis(acetylacetonato)(1,5-hexadiene) ruthenium(II) (Hereinafter, Referred to as "[Ru(acac)$_2$ (hd)]")

In a 100 mL-volume flask equipped with a stirrer, a thermometer and a dropping funnel were placed 8.87 g (33.9 mmol) of ruthenium trichloride trihydrate, 6.12 g (74.5 mmol) of 1,5-hexadiene, and 60 mL of isopropyl alcohol. And then, the resulting mixture was reacted at a temperature of 70° C. while stirring for 4 hours. Subsequently, an aqueous solution comprising 10.6 g (106 mmol) of acetylacetone and 4.22 g (106 mmol) of sodium hydroxide was dropped into the flask, and the resulting mixture was reacted while stirring for 0.5 hours. After the completion of the reaction, 60 mL of methylcyclohexane and 30 mL of water were added to the resulting mixture, and the organic layer was separated and dried with anhydrous sodium sulfate. After the filtration of the organic layer, the filtrate was concentrated, and the concentrate was distilled under reduced pressure (140° C., 39 Pa), to give a yellow-brown viscous liquid. The obtained liquid was purified with silica gel column chromatography (developing solvent: hexane/ethyl acetate=9/1 (volume ratio)), to give 10.3 g of bis(acetylacetonato)(1,5-hexadiene)ruthenium(II) as a yellow-brown viscous liquid (isolation yield: 80%).

The obtained bis(acetylacetonato)(1,5-hexadiene)ruthenium(II) is a novel compound and had the following properties:

IR (neat (cm$^{-1}$)): 3076, 2923, 1576, 1517, 1400, 1268, 1201, 1022, 933, 767, 620, 432.

(The peak characteristic of β-diketone (1622 cm$^{-1}$) disappeared and the peak characteristic of β-diketonato (1576 cm$^{-1}$) was observed.)

Elemental Analysis (C$_{16}$H$_{24}$O$_4$Ru): carbon: 50.2%, hydrogen: 6.45%, ruthenium: 26.3%.

(Theoretical value: carbon: 50.4%, hydrogen: 6.34%, ruthenium: 26.5%)

MS (m/e): 382, 300, 43.

Examples 2-2-2-4

Vapor-Deposition Test

Formation of Metallic Ruthenium Thin Film

The vapor-deposition tests were conducted on the organoruthenium complex obtained in Example 2-1 ([Ru(acac)$_2$ (hd)]) by the CVD method to evaluate the film-forming properties.

The apparatus shown in FIG. 1 was used to conduct the evaluation tests. The ruthenium complex 20 in a vaporizer (glass ampule) 3 is heated and vaporized by a heater 10B. The vaporized ruthenium complex 20 is discharged from the vaporizer 3, together with a helium gas which is fed into the vaporizer 3 via a mass flow controller 1A after pre-heating by a pre-heater 10A. The gas discharged from the vaporizer 3 is fed into a reactor 4, together with a hydrogen gas (Example 2-2) or an oxygen gas (Example 2-3) which is fed via a mass flow controller 1B and a stop valve 2. In Example 2-4, the valve 2 is closed, and neither a hydrogen gas nor an oxygen gas is fed into the reactor 4. The pressure in the reaction system (the reactor) is controlled to a predetermined pressure by opening and closing a valve 6 arranged upstream of a vacuum pump, and is monitored by a pressure gage 5. The central part of the glass reactor can be heated by a heater 10C. The ruthenium complex introduced into the reactor is reduced on the surface of the substrate 21 which is disposed in the central part of the reactor and heated to a predetermined temperature by the heater 10C, thereby depositing a metallic ruthenium thin film on the substrate 21. The gas discharged from the reactor 4 is exhausted to the atmosphere via a trap 7 and the vacuum pump.

The vapor-deposition conditions and results (film properties) are shown in Table 3. The rectangular substrate of 7 mm×40 mm was used as the substrate on which the film was to be vapor-deposited.

TABLE 3

| | Vapor-deposition conditions | Film properties |
|---|---|---|
| Example 2-2 | Ru complex: [Ru(acac)$_2$(hd)]<br>Ru complex vaporization temp.: 140° C.<br>He carrier gas flow rate: 30 ml/min.<br>Hydrogen flow rate: 120 ml/min.<br>Substrate material: SiO$_2$/Si<br>Substrate temp.: 250° C.<br>Pressure in the reactor: 7980 Pa<br>Vapor-deposition time: 30 min. | Film thickness:<br>30 nm<br>XPS analysis:<br>Metallic ruthenium film |
| Example 2-3 | Ru complex: [Ru(acac)$_2$(hd)]<br>Ru complex vaporization temp.: 70° C.<br>He carrier gas flow rate: 40 ml/min.<br>Oxygen flow rate: 10 ml/min.<br>Substrate material: SiO$_2$/Si<br>Substrate temp.: 250° C.<br>Pressure in the reactor: 900 Pa<br>Vapor-deposition time: 30 min. | Film thickness:<br>60 nm<br>XPS analysis:<br>Metallic ruthenium film |
| Example 2-4 | Ru complex: [Ru(acac)$_2$(hd)]<br>Ru complex vaporization temp.: 70° C.<br>He carrier gas flow rate: 40 ml/min.<br>Substrate material: SiO$_2$/Si<br>Substrate temp.: 250° C.<br>Pressure in the reactor: 900 Pa<br>Vapor-deposition time: 30 min. | Film thickness:<br>30 nm<br>XPS analysis:<br>Metallic ruthenium film |

The results indicate that the organoruthenium complex ([Ru(acac)$_2$ (hd)]) has the excellent metallic ruthenium film-forming properties at a low temperature in the hydrogen reducing atmosphere, in the oxygen atmosphere, or under the thermal decomposition reaction conditions.

Example 3-1

Preparation of bis(acetylacetonato)(1,3-pentadiene)ruthenium(II) (Hereinafter, Referred to as "[Ru(acac)$_2$ (pd)]")

In a 100 mL-volume flask equipped with a stirrer, a thermometer and a dropping funnel were placed 5.52 g (21.1 mmol) of ruthenium trichloride trihydrate, 4.03 g (59.2 mmol) of 1,3-pentadiene, and 60 mL of isopropyl alcohol. And then, the resulting mixture was reacted at a temperature of 50° C. while stirring for 6 hours. Subsequently, an aqueous solution comprising 6.64 g (66.3 mmol) of acetylacetone and 2.60 g (65 mmol) of sodium hydroxide was dropped into the flask, and the resulting mixture was reacted while stirring for 0.5 hours. After the completion of the reaction, 30 mL of methylcyclohexane and 10 mL of water were added to the resulting mixture, and the organic layer was separated and dried with anhydrous sodium sulfate. After the filtration of the organic layer, the filtrate was concentrated, and the concentrate was distilled under reduced pressure (140° C., 41 Pa), to give a yellow-brown viscous liquid. The obtained liquid was purified with silica gel column chromatography (developing solvent: hexane/ethyl acetate=9/1 (volume ratio)), to give 2.33 g of bis(acetylacetonato)(1,3-pentadiene)ruthenium(II) as a yellow-brown viscous liquid (isolation yield: 30%).

The obtained bis(acetylacetonato)(1,3-pentadiene)ruthenium(II) is a novel compound and had the following properties:

IR (neat (cm$^{-1}$)): 3076, 2968, 2920, 1574, 1517, 1399, 1267, 1203, 1023, 967, 933, 770, 608, 443.
(The peak characteristic of β-diketone (1622 cm$^{-1}$) disappeared and the peak characteristic of β-diketonato (1574 cm$^{-1}$) was observed.)

Elemental Analysis ($C_{15}H_{22}O_4Ru$): carbon: 49.1%, hydrogen: 6.10%, ruthenium: 27.6%.
(Theoretical value: carbon: 49.0%, hydrogen: 6.04%, ruthenium: 27.5%)

MS (m/e): 368, 300, 43.

Examples 3-2-3-3

Vapor-Deposition Test

Formation of Metallic Ruthenium Thin Film

The vapor-deposition tests were conducted on the organoruthenium complex obtained in Example 3-1 ([Ru(acac)$_2$ (pd)]) by the CVD method to evaluate the film-forming properties.

The apparatus shown in FIG. 1 was used to conduct the evaluation tests. The ruthenium complex 20 in a vaporizer (glass ampule) 3 is heated and vaporized by a heater 10B. The vaporized ruthenium complex 20 is discharged from the vaporizer 3, together with a helium gas which is fed into the vaporizer 3 via a mass flow controller 1A after pre-heating by a pre-heater 10A. The gas discharged from the vaporizer 3 is fed into a reactor 4. (In Example 3-2, the gas discharged from the vaporizer 3 is fed into the reactor 4, together with a hydrogen gas which is fed via a mass flow controller 1B and a stop valve 2.) The pressure in the reaction system (the reactor) is controlled to a predetermined pressure by opening and closing a valve 6 arranged upstream of a vacuum pump, and is monitored by a pressure gage 5. The central part of the glass reactor can be heated by a heater 10C. The ruthenium complex introduced into the reactor is reduced on the surface of the substrate 21 which is disposed in the central part of the reactor and heated to a predetermined temperature by the heater 10C, thereby depositing a metallic ruthenium thin film on the substrate 21. The gas discharged from the reactor 4 is exhausted to the atmosphere via a trap 7 and the vacuum pump.

The vapor-deposition conditions and results (film properties) are shown in Table 4. The rectangular substrate of 7 mm×40 mm was used as the substrate on which the film was to be vapor-deposited.

TABLE 4

| | Vapor-deposition conditions | Film properties |
|---|---|---|
| Example 3-2 | Ru complex: [Ru(acac)$_2$(pd)]<br>Ru complex vaporization temp.: 140° C.<br>He carrier gas flow rate: 30 ml/min.<br>Hydrogen flow rate: 120 ml/min.<br>Substrate material: SiO$_2$/Si<br>Substrate temp.: 250° C.<br>Pressure in the reactor: 7980 Pa<br>Vapor-deposition time: 30 min. | Film thickness:<br>30 nm<br>XPS analysis:<br>Metallic ruthenium<br>film |
| Example 3-3 | Ru complex: [Ru(acac)$_2$(pd)]<br>Ru complex vaporization temp.: 70° C.<br>He carrier gas flow rate: 40 ml/min.<br>Substrate material: SiO$_2$/Si<br>Substrate temp.: 300° C.<br>Pressure in the reactor: 798 Pa<br>Vapor-deposition time: 30 min. | Film thickness:<br>30 nm<br>XPS analysis:<br>Metallic ruthenium<br>film |

The results indicate that the organoruthenium complex ([Ru(acac)$_2$ (pd)]) has the excellent metallic ruthenium film-forming properties at a low temperature in the hydrogen reducing atmosphere, or in the absence of hydrogen.

Reference Example 4-1

Preparation of bis(6-methyl-2,4-heptanedionato)(1,5-hexadiene)ruthenium(II) [In the general formula (4-1), $X^4$: methyl; $Y^4$: isobutyl; $Z^4$: hydrogen atom] (Hereinafter, Referred to as "[Ru(mhd)$_2$ (hd)]")

In a 100 mL-volume flask equipped with a stirrer, a thermometer and a dropping funnel were placed 3.23 g (12.4 mmol) of ruthenium trichloride trihydrate, 3.00 g (36.5 mmol) of 1,5-hexadiene, and 20 mL of isopropyl alcohol. And then, the resulting mixture was stirred at a temperature of 60° C. for 4 hours. Subsequently, an aqueous solution comprising 5.55 g (39.0 mmol) of 6-methyl-2,4-heptanedione and 1.51 g (37.8 mmol) of sodium hydroxide was dropped into the flask, and the resulting mixture was reacted while stirring for 0.5 hours. After the completion of the reaction, 30 mL of hexane and 30 mL of water were added to the resulting mixture, and the organic layer was separated and dried with anhydrous sodium sulfate. After the filtration of the organic layer, the filtrate was concentrated, and the concentrate was distilled under reduced pressure (170° C., 45 Pa), to give a yellow-brown viscous liquid. The obtained liquid was purified with silica gel column chromatography (developing solvent: hexane/ethyl acetate=9/1 (volume ratio)), to give 2.30 g of bis(6-methyl-2,4-heptanedionato)(1,5-hexadiene)ruthenium(II) as a yellow-brown viscous liquid (isolation yield: 40%).

The obtained bis(6-methyl-2,4-heptanedionato)(1,5-hexadiene)ruthenium(II) had the following properties:

IR (neat (cm$^{-1}$)): 2955, 2869, 1574, 1516, 1412, 1367, 1254, 1190, 1167, 1025, 967, 922, 769, 625.
(The peak characteristic of β-diketone of 6-methyl-2,4-heptanedione (1614 cm$^{-1}$) disappeared and the peak characteristic of β-diketonato (1574 cm$^{-1}$) was observed.)

Elemental Analysis (C$_{22}$H$_{36}$O$_4$Ru): carbon: 56.9%, hydrogen: 7.80%, ruthenium: 21.6%.
(Theoretical value: carbon: 56.8%, hydrogen: 7.79%, ruthenium: 21.7%)

Example 4-1

Vapor-Deposition Test

Formation of Metallic Ruthenium Film

The vapor-deposition tests were conducted on the organoruthenium complex obtained in Reference Example 4-1 ([Ru(mhd)$_2$ (hd)]) by the CVD method to evaluate the film-forming properties.

The apparatus shown in FIG. 1 was used to conduct the evaluation tests. The ruthenium complex 20 in a vaporizer (glass ampule) 3 is heated and vaporized by a heater 10B. The vaporized ruthenium complex 20 is discharged from the vaporizer 3, together with a helium gas which is fed into the vaporizer 3 via a mass flow controller 1A after pre-heating by a pre-heater 10A. The gas discharged from the vaporizer 3 is fed into a reactor 4, together with a hydrogen gas which is fed via a mass flow controller 1B and a stop valve 2. The pressure in the reaction system (the reactor) is controlled to a predetermined pressure by opening and closing a valve 6 arranged upstream of a vacuum pump, and is monitored by a pressure gage 5. The central part of the glass reactor can be heated by a heater 10C. The ruthenium complex introduced into the reactor is reduced on the surface of the substrate 21 which is disposed in the central part of the reactor and heated to a predetermined temperature by the heater 10C, thereby depositing a metallic ruthenium thin film on the substrate 21. The gas discharged from the reactor 4 is exhausted to the atmosphere via a trap 7 and the vacuum pump.

The vapor-deposition conditions and results (film properties) are shown in Table 5. The rectangular substrate of 7 mm×40 mm was used as the substrate on which the film was to be vapor-deposited.

TABLE 5

| | Vapor-deposition conditions | Film properties |
|---|---|---|
| Example 4-1 | Ru complex: [Ru(mhd)$_2$(hd)]<br>Ru complex vaporization temp.: 165° C.<br>He carrier gas flow rate: 30 ml/min.<br>Hydrogen flow rate: 120 ml/min.<br>Substrate material: SiO$_2$/Si<br>Substrate temp.: 270° C.<br>Pressure in the reactor: 7980 Pa<br>Vapor-deposition time: 30 min. | Film thickness:<br>20 nm<br>XPS analysis:<br>Metallic ruthenium<br>film |

The results indicate that the organoruthenium complex ([Ru(mhd)$_2$ (hd)]) has the excellent metallic ruthenium film-forming properties at a low temperature in the hydrogen reducing atmosphere.

INDUSTRIAL APPLICABILITY

According to the present invention, there can be provided an organoruthenium complex which has a low melting point, excellent stability against moisture, air and heat, and is suitable for the film formation by a CVD method. There can be also provided a method for producing a ruthenium-containing thin film using the organoruthenium complex.

Furthermore, according to the present invention, there can be provided bis(acetylacetonato)(1,5-hexadiene)ruthenium and bis(acetylacetonato)(1,3-pentadiene)ruthenium. There can be also provided a method for producing a metallic ruthenium-containing thin film, using at least one of these ruthenium complexes, by a chemical vapor deposition method.

Furthermore, according to the present invention, there can be provided a method for producing a metallic ruthenium-containing thin film, using an organoruthenium complex comprising a β-diketonato and an unsaturated hydrocarbon compound having at least two double bonds as a ligand, by a chemical vapor deposition method.

The invention claimed is:

1. An organoruthenium complex comprising a β-diketonato having an alkoxyalkylmethyl group and an unsaturated hydrocarbon compound having at least two double bonds as a ligand, and represented by the general formula (1-1):

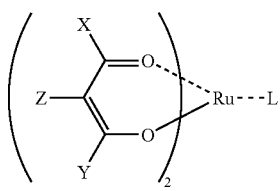

(1-1)

wherein X represents a group represented by the general formula (1-2):

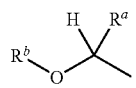

(1-2)

wherein $R^a$ and $R^b$ independently represent a linear or branched alkyl group having 1 to 5 carbon atoms;
Y represents a group represented by the above general formula (1-2), or a linear or branched alkyl group having 1 to 8 carbon atoms;
Z represents a hydrogen atom, or an alkyl group having 1 to 4 carbon atoms; and
L represents an unsaturated hydrocarbon compound having at least two double bonds.

2. The organoruthenium complex as claimed in claim 1, wherein the unsaturated hydrocarbon compound having at least two double bonds is 1,5-hexadiene, 1,5-cyclooctadiene, norbornadiene, 4-vinyl-1-cyclohexene or 1,3-pentadiene.

3. A method for producing a ruthenium-containing thin film comprising:
a) providing the organoruthenium complex as claimed in claim 1 or a solvent solution thereof as a ruthenium source, and
b) forming the ruthenium-containing thin film by a chemical vapor deposition method.

4. A method for producing a ruthenium-containing thin film comprising:
a) providing the organoruthenium complex as claimed in claim 1 or a solvent solution thereof, and a hydrogen source, and
b) forming the ruthenium-containing thin film by a chemical vapor deposition method.

5. The method for producing a ruthenium-containing thin film as claimed in claim 4, wherein the hydrogen source is a hydrogen gas.

6. A method for producing a ruthenium-containing thin film comprising:
a) providing the organoruthenium complex as claimed in claim 1 or a solvent solution thereof, and an oxygen source, and
b) forming the ruthenium-containing thin film by a chemical vapor deposition method.

7. The method for producing a ruthenium-containing thin film as claimed in claim 6, wherein the oxygen source is an oxygen gas.

8. The method for producing a ruthenium-containing thin film as claimed in claim 6, wherein the ruthenium-containing thin film produced is a metallic ruthenium film which contains substantially no oxygen atom.

9. The method for producing a ruthenium-containing thin film as claimed in claim 3, wherein the solvent used is at least one selected from the group consisting of aliphatic hydrocarbons, aromatic hydrocarbons, and ethers.

10. Bis(acetylacetonato)(1,5-hexadiene)ruthenium represented by the formula (2-1):

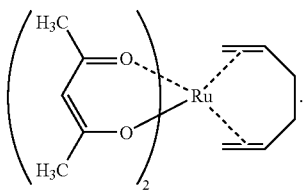

(2-1)

11. A method for producing a metallic ruthenium-containing thin film comprising:
a) providing Bis(acetylacetonato)(1,5-hexadiene)ruthenium as claimed in claim 10, and
b) forming the metallic ruthenium-containing thin film by a chemical vapor deposition method.

12. A method for producing a ruthenium-containing thin film comprising:
a) providing bis(acetylacetonato)(1,5-hexadiene)ruthenium as claimed in claim 10 or a solvent solution thereof as a ruthenium source, and
b) forming the ruthenium-containing thin film by a chemical vapor deposition method.

13. A method for producing a ruthenium-containing thin film comprising:
a) providing bis(acetylacetonato)(1,5-hexadiene)ruthenium as claimed in claim 10 or a solvent solution thereof, and a hydrogen source and
b) forming the ruthenium-containing thin film by a chemical vapor deposition method.

14. The method for producing a ruthenium-containing thin film as claimed in claim 13, wherein the hydrogen source is a hydrogen gas.

15. A method for producing a ruthenium-containing thin film comprising:
a) providing bis(acetylacetonato)(1,5-hexadiene)ruthenium as claimed in claim 10 or a solvent solution thereof, and an oxygen source, and
b) forming the ruthenium-containing thin film by a chemical vapor deposition method.

16. The method for producing a ruthenium-containing thin film as claimed in claim 15, wherein the oxygen source is an oxygen gas.

17. The method for producing a ruthenium-containing thin film as claimed in claim 15, wherein the ruthenium-containing thin film produced is a metallic ruthenium film which contains substantially no oxygen atom.

18. The method for producing a ruthenium-containing thin film as claimed in claim 12, wherein the solvent used is at least one selected from the group consisting of aliphatic hydrocarbons, aromatic hydrocarbons, and ethers.

19. Bis(acetylacetonato)(1,3-pentadiene)ruthenium represented by the formula (3-1):

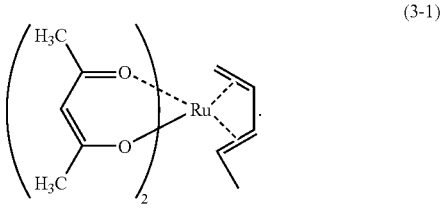

(3-1)

20. A method for producing a metallic ruthenium-containing thin film comprising:
    a) providing Bis(acetylacetonato)(1,3-pentadiene}ruthenium as claimed in claim 19, and
    b) forming the metallic ruthenium-containing thin film by a chemical vapor deposition method.

21. A method for producing a ruthenium-containing thin film comprising:
    a) providing bis(acetylacetonato)(1,3-pentadiene)ruthenium as claimed in claim 19 or a solvent solution thereof as a ruthenium source, and
    b) forming the ruthenium-containing thin film by a chemical vapor deposition method.

22. A method for producing a ruthenium-containing thin film comprising:
    a) providing bis(acetylacetonato)(1,3-pentadiene)ruthenium as claimed in claim 19 or a solvent solution thereof, and a hydrogen source are used and
    b) forming the ruthenium-containing thin film by a chemical vapor deposition method.

23. The method for producing a ruthenium-containing thin film as claimed in claim 22, wherein the hydrogen source is a hydrogen gas.

24. A method for producing a ruthenium-containing thin film comprising:
    a) providing bis(acetylacetonato)(1,3-pentadiene)ruthenium as claimed in claim 19 or a solvent solution thereof, and an oxygen source, and
    b) forming the ruthenium-containing thin film by a chemical vapor deposition method.

25. The method for producing a ruthenium-containing thin film as claimed in claim 24, wherein the oxygen source is an oxygen gas.

26. The method as claimed in claim 21, wherein the solvent used is at least one selected from the group consisting of aliphatic hydrocarbons, aromatic hydrocarbons, and ethers.

27. A method for producing a metallic ruthenium-containing thin film comprising
    a) providing a ruthenium source and a hydrogen source wherein the ruthenium source is an organoruthenium complex comprising a β-diketonato and an unsaturated hydrocarbon compound having at least two double bonds as a ligand, and represented by the general formula (4-1):

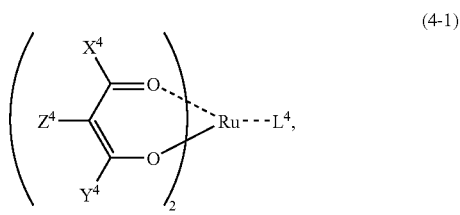

(4-1)

wherein $X^4$ and $Y^4$ independently represent a linear or branched alkyl group (with the proviso that the sum total of the carbon atoms in the groups represented by $X^4$ and $Y^4$ is 2 to 10);
    $Z^4$ represents a hydrogen atom, or an alkyl group having 1 to 4 carbon atoms; and
    $L^4$ represents an unsaturated hydrocarbon compound having at least two double bonds, or a solvent solution thereof; and
    b) forming the ruthenium-containing thin film by a chemical vapor deposition method.

28. The method as claimed in claim 27, wherein the unsaturated hydrocarbon compound having at least two double bonds is 1,5-hexadiene, 1,5-cyclooctadiene, norbornadiene, 4-vinyl-1-cyclohexene or 1,3-pentadiene.

29. The method as claimed in claim 27, wherein the hydrogen source is a hydrogen gas.

30. A method for producing a ruthenium-containing thin film comprising:
    a) providing a ruthenium source and an oxygen source, wherein the ruthenium source is an organoruthenium complex comprising a 8-diketonato and an unsaturated hydrocarbon compound having at least two double bonds as a ligand, and represented by the above general formula (4-1), or a solvent solution thereof; and
    b) forming the ruthenium-containing thin film by a chemical vapor deposition method.

31. The method as claimed in claim 30, wherein the oxygen source is an oxygen gas.

32. The method as claimed in claim 27, wherein the solvent used is at least one selected from the group consisting of aliphatic hydrocarbons, aromatic hydrocarbons, and ethers.

33. The method as claimed in claim 30, wherein the solvent used comprises at least one selected from the group consisting of aliphatic hydrocarbons, aromatic hydrocarbons, and ethers.

* * * * *